United States Patent
Hoan

(10) Patent No.: US 12,121,354 B2
(45) Date of Patent: *Oct. 22, 2024

(54) TUBING SYSTEM FOR USE IN A BLOOD SAMPLING-BLOOD PRESSURE MONITORING SYSTEM

(71) Applicant: Edwards Lifesciences Corporation, Irvine, CA (US)

(72) Inventor: Andrew Nguyen Hoan, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 174 days.

This patent is subject to a terminal disclaimer.

(21) Appl. No.: 17/860,026

(22) Filed: Jul. 7, 2022

(65) Prior Publication Data

US 2022/0338771 A1 Oct. 27, 2022

Related U.S. Application Data

(63) Continuation of application No. 16/422,493, filed on May 24, 2019, now Pat. No. 11,382,543.

(Continued)

(51) Int. Cl.
*A61B 5/00* (2006.01)
*A61B 5/15* (2006.01)
(Continued)

(52) U.S. Cl.
CPC .... *A61B 5/150992* (2013.01); *A61B 5/15003* (2013.01); *A61B 5/150221* (2013.01);
(Continued)

(58) Field of Classification Search
CPC .......... A61B 5/150992; A61B 5/15003; A61B 5/150221; A61B 5/022; A61B 5/150351; A61B 5/150389; A61B 5/150572; A61B 5/153; A61B 5/0215; A61B 5/6866; A61M 39/08
See application file for complete search history.

(56) References Cited

U.S. PATENT DOCUMENTS 2,804,075 A 8/1957 Borden
2,830,361 A 4/1958 Bruner
(Continued)

FOREIGN PATENT DOCUMENTS

| CA | 2073402 C | 1/1999 |
| DE | 19949590 A1 | 6/2000 |
| DE | 102009037045 A1 | 2/2011 |

OTHER PUBLICATIONS

Joseph, Dr. Tinku, "Arterial Lines," Published on Jun. 10, 2016.

*Primary Examiner* — May A Abouelela

(57) ABSTRACT

Disclosed is a tubing system for use in a blood sampling-blood pressure monitoring system. The blood sampling-blood pressure monitoring system may include a control valve, a reservoir with a plunger, a sampling site, and a blood pressure transducer for measuring the blood pressure of a patient. The tubing system may comprise: a plurality of flexible tubing sections and a plurality of rigid tubing sections. The plurality of rigid tubing sections and flexible tubing sections may be interlinked with one another between the patient and the blood pressure transducer for the blood pressure measurement of the patient.

18 Claims, 3 Drawing Sheets

Related U.S. Application Data

(60) Provisional application No. 62/683,102, filed on Jun. 11, 2018.

(51) Int. Cl.
*A61B 5/022* (2006.01)
*A61B 5/153* (2006.01)

(52) U.S. Cl.
CPC ......... *A61B 5/022* (2013.01); *A61B 5/150351* (2013.01); *A61B 5/150389* (2013.01); *A61B 5/150572* (2013.01); *A61B 5/153* (2013.01)

(56) References Cited

U.S. PATENT DOCUMENTS

| | | | |
|---|---|---|---|
| 4,246,899 A * | 1/1981 | Loseff | A61M 1/77 604/97.02 |
| 4,250,872 A | 2/1981 | Tamari | |
| 5,334,171 A | 8/1994 | Kaldany | |
| 5,361,756 A | 11/1994 | Cernosek et al. | |
| 6,240,231 B1 | 5/2001 | Ferrera et al. | |
| 6,652,508 B2 | 11/2003 | Griffin et al. | |
| 6,817,983 B1 | 11/2004 | Millar | |
| 7,300,534 B2 | 11/2007 | Wang et al. | |
| 9,669,187 B2 | 6/2017 | Tjassens et al. | |
| 2006/0188407 A1* | 8/2006 | Gable | A61B 5/0084 604/19 |
| 2006/0189926 A1* | 8/2006 | Hall | A61B 5/150213 600/316 |
| 2007/0142729 A1* | 6/2007 | Pfeiffer | A61M 25/0097 600/487 |
| 2007/0179407 A1* | 8/2007 | Gordon | A61B 5/15003 604/401 |
| 2008/0200837 A1* | 8/2008 | Frazier | A61B 5/150236 600/573 |
| 2008/0275354 A1* | 11/2008 | Thuramalla | A61B 5/0275 604/4.01 |
| 2009/0124964 A1* | 5/2009 | Leach | G16H 10/40 604/66 |
| 2009/0156922 A1* | 6/2009 | Goldberger | A61B 5/15087 600/573 |
| 2009/0156975 A1* | 6/2009 | Robinson | A61B 5/4839 210/636 |
| 2010/0240964 A1* | 9/2010 | Sterling | A61B 5/150221 600/300 |
| 2011/0313318 A1* | 12/2011 | Rule | A61B 5/150389 600/581 |
| 2012/0050994 A1 | 3/2012 | Boday et al. | |
| 2012/0065482 A1* | 3/2012 | Robinson | A61B 5/150389 600/309 |
| 2012/0123298 A1* | 5/2012 | Mendels | A61B 5/150862 600/579 |
| 2013/0180339 A1* | 7/2013 | Brugger | A61B 5/0215 73/700 |
| 2014/0236120 A1* | 8/2014 | Tsai | A61M 25/0138 604/528 |
| 2014/0276117 A1 | 9/2014 | Burkett | |
| 2015/0119663 A1* | 4/2015 | Lim | A61B 5/1427 600/309 |
| 2017/0020427 A1* | 1/2017 | Rogers | A61B 5/150473 |
| 2017/0027458 A1* | 2/2017 | Glover | A61B 5/6851 |
| 2017/0056032 A1 | 3/2017 | Look et al. | |
| 2017/0296112 A1* | 10/2017 | Lim | G01N 21/07 |
| 2018/0271425 A1* | 9/2018 | Rogers | A61B 5/15074 |
| 2018/0306831 A1* | 10/2018 | Hatamian | A61B 5/02 |
| 2019/0021674 A1* | 1/2019 | Brewer, Jr. | A61P 3/06 |
| 2019/0374147 A1* | 12/2019 | Hoan | A61M 39/08 |

\* cited by examiner

US 12,121,354 B2

TUBING SYSTEM FOR USE IN A BLOOD SAMPLING-BLOOD PRESSURE MONITORING SYSTEM

CROSS-REFERENCE TO RELATED APPLICATIONS

This application is a continuation of U.S. patent application Ser. No. 16/422,493, which was filed on May 24, 2019, and entitled "Tubing System For Use In A Blood Sampling-Blood Pressure Monitoring System," which claims the benefit of U.S. Provisional Patent Application No. 62/683,102 filed Jun. 11, 2018, which is incorporated by reference herein in its entirety.

BACKGROUND

Field

The present invention relates to a tubing system, and, in particular, to a tubing system for use in a blood sampling-blood pressure measurement system.

Relevant Background

In a hospital setting there is always the need to monitor patient health through the evaluation of a blood chemistry profile. The simplest method employed in the hospital is to use a syringe carrying a sharpened cannula at one end and insert that cannula into a vein or artery to extract a blood sample from the patient. Patients that are in critical care units or the operating room sometimes require as many as twelve samples a day. Such frequent sampling injections potentially expose the patient to airborne bacteria and viruses which can enter the bloodstream through the opening made by the sharpened cannula.

One way to obtain a blood sample is to draw the blood from a catheter that is already inserted in the patient, either in a central venous line, such as one placed in the right atrium, or in an arterial line. Typically, existing access sites for arterial or venous or pressure monitoring lines are used to take periodic blood samples from the patient. Conventional mechanisms for drawing blood from the lines used for infusion or pressure monitoring utilize a plurality of stopcock mechanisms that preclude flow from the infusion fluid supply or from the pressure column drip supply, while allowing blood to flow from the patient into a collecting syringe connected to a proximal port formed in one of the stopcocks.

Earlier systems required a two-step operation where a first sample of fluid, generally about 5 ml in volume for intensive care environments was withdrawn into the sampling syringe and discarded. This first sample potentially included some of the infusion fluid and thus would be an unreliable blood chemistry measurement sample. After the initial sample had been discharged, the second sample was pure blood from the artery or vein.

In response to the drawbacks associated with earlier two-step sampling systems, closed systems were developed. Commercial closed systems such as the Venous Arterial blood Management Protection (VAMP) system feature a reservoir in the tubing line from the patient that can draw fluid past a sampling port. The clearing volume is held in the in-line reservoir, and set-aside in a syringe for re-infusion later. The sampling systems are often used in conjunction with a pressure monitor having a transducer continuously or periodically sensing pressure within the sampling line except during the draw of a blood sample.

The VAMP system conveniently utilizes a reservoir with one-handed operability, and includes a line from the patient into and out of the reservoir and to a proximal source of flushing fluid and a pressure transducer. (The standard directional nomenclature is that proximal is toward the clinician, or away from the patient, and distal is toward the patient). A pressure transducer in the line proximal to the reservoir senses fluid pressure within the line and conveys the signal to a monitor. One exemplary pressure transducer is a Disposable Pressure Transducer (DPT).

When a blood sample is to be taken, the nurse or clinician withdraws an amount of fluid into the reservoir chamber and distal line sufficient to pull pure blood past one or more fluid sampling sites. After full retraction of the plunger, the stopcock valve closes off the reservoir from the patient and a sample of blood is taken at one or more of the sampling sites. Subsequently, the clinician manipulates the stopcock valve so that the volume within the reservoir can be re-infused back into the patient by depressing the plunger, and the flushing drip and pressure monitoring resumes.

Tubes that are currently utilized in blood pressure monitoring systems (and in combined blood pressure monitoring systems and blood sampling systems) are typically soft (for compliance) and long in length. Unfortunately, this soft and long tubing configuration attenuates the signal from the patient to the pressure transducer which reduces the accuracy of the blood pressure measurement.

DETAILED DESCRIPTION

Figure 1:
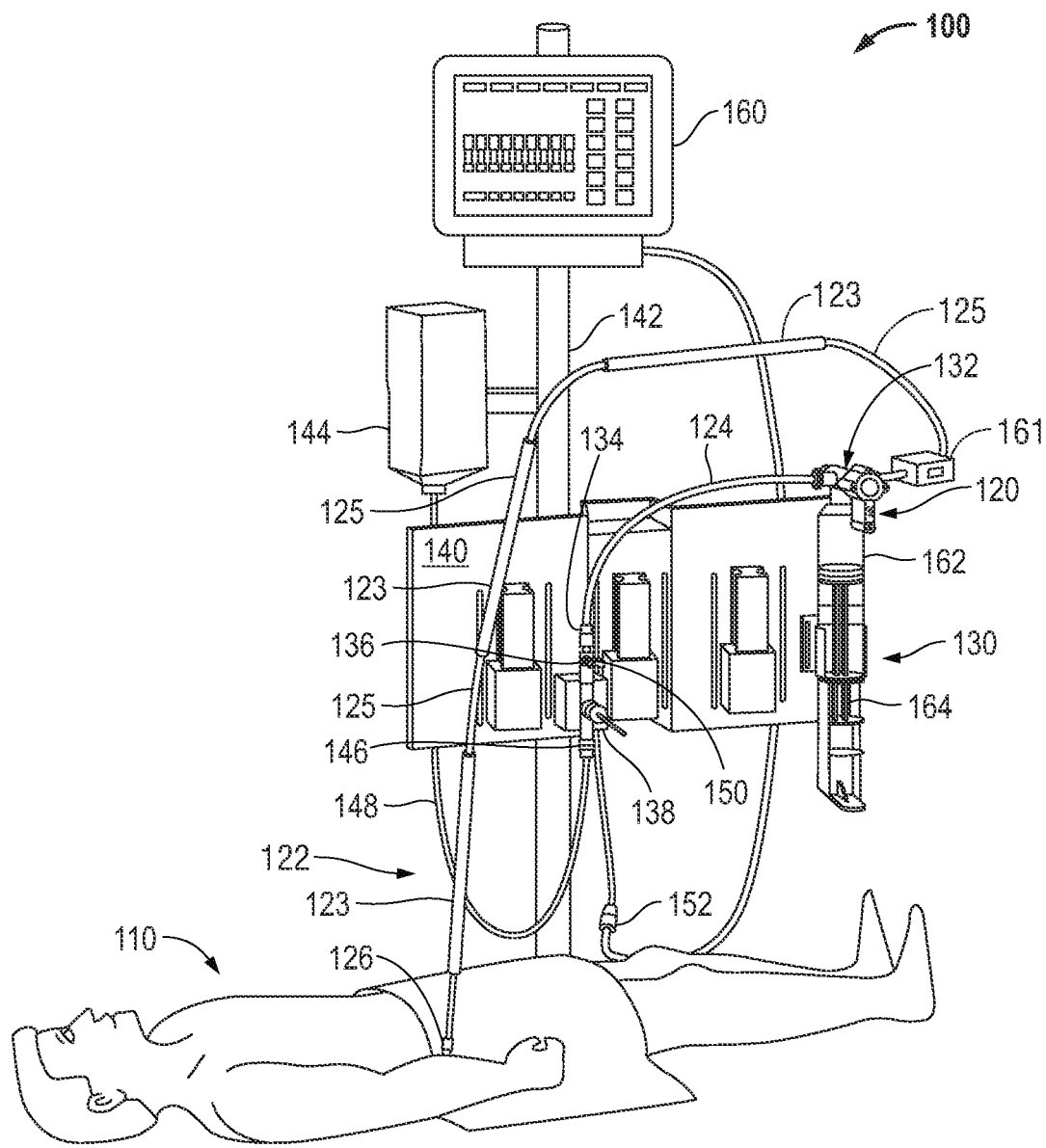
FIG. 1 is a diagram illustrating an example blood sampling-blood pressure monitoring system as may be set up in a hospital room and connected to a patient with flexible and rigid tubing sections, according to embodiments of the invention.

FIG. 1 illustrates an example blood sampling system 120 in an example blood sampling-blood pressure monitoring system 100 as may be set up in a hospital room and connected to a patient 110. The blood sampling system 120 comprises a conduit line having a distal segment 122 toward the patient 110 and a proximal segment 124. The distal segment 122 may terminate in a male luer connector 126 for attaching to a female luer connector (not shown) of an injection site, or other conduit leading to the patient 110. A reservoir 130 connects to the conduit line via a multi-port control valve 132 interposed between the distal segment 122 and the proximal segment 124. The multi-port control valve 132 externally resembles a stopcock and controls fluid flow between the conduit line and the reservoir 130.

The proximal segment 124 extends from the multi-port control valve 132 and terminates in a female luer connector 134 attached to a stopcock 136 of a pressure transducer 138 (e.g., a disposable pressure transducer (DPT)). The reservoir 130 and pressure transducer 138 removably mount to a bracket 140 which, in turn, may be secured to a conventional pole support 142 with the reservoir 130 in a vertical orientation.

As mentioned above, the blood sampling system 120 forms a portion of the blood sampling-blood pressure monitoring system 100, and the pressure transducer 138 may be a DPT. However, it should be appreciated that any type of pressure monitoring device may be utilized.

A supply of flush solution 144 connects to a flush port 146 of the transducer 138 via tubing 148. Typically, the flush solution 144 comprises a bag of physiological fluid such as saline surrounded by a pressurized sleeve that squeezes the fluid and forces it through the tubing 148. In addition, an infusion fluid supply (not shown) may be provided in communication with an infusion port 150 of the stopcock 136. The pressure transducer 138 is thus placed in fluid communication with the arterial or venous system of the patient 110 through the conduit line, and includes a cable and plug 152 to connect to a suitable display monitor (e.g., patient monitor 160). The pressure transducer 138 is shown positioned within the proximal segment 124.

A fluid sampling site 161 that includes a Z-shaped flow passage adjacent a pre-slit septum may be utilized to sample blood. The septum preferably comprises an elastomeric disc which accepts a blunt cannula and reseals after each sample is drawn, reducing the potential for contamination and eliminating the danger of needle sticks. However, any type of fluid sampling site may be utilized.

The blood sampling reservoir 130 may include a syringe-type variable volume chamber 162, though other reservoirs that have constant volume chambers or other receptacles for receiving fluid may be used. The reservoir 130 is of a type that includes a channel through the variable volume chamber 162 for passage of flushing fluid therethrough.

As an example, a clinician may rotate a valve handle of the multi-port control valve 132 to select a mode of operation (e.g., a monitoring mode, a drawing/re-infusing mode, a sampling mode, or a flushing/priming mode). In the monitoring mode, the pressure transducer 138 may continuously or periodically sense pressure within the sampling line to measure the patient's blood pressure and forwards the signal to the display monitor 160. In the drawing mode, the plunger 164 of the reservoir 130 may draw a fluid sample into the chamber 162 of the reservoir 130 to draw blood from the patient 110 past the sampling site 161. In the sampling mode, the clinician may take a sample of undiluted blood from the sampling site 161. In the re-infusing mode, the clinician may depress the plunger 164 to re-infuse blood and fluid from the reservoir 130 and tubes back to the patient 110. In the flushing/priming mode, the reservoir 130, sample sites 161, and tubes can be flushed, cleared, and de-bubbled such that portions of the blood sampling-blood pressure monitoring system 100 may be cleared for operation. In particular, in this mode, a supply of flush solution 144 connects to a flush port 146 of the transducer 138 via tubing 148 and can be flushed through the reservoir 130, sample sites 161, and tubes for flushing and clearing.

As an example in the drawing mode, a reduced pressure is created within the variable volume chamber 162 by withdrawing the plunger 164 such that a fluid sample from the distal segment 122 is drawn into the chamber 162. The chamber 162 may have a sufficient volume, e.g., 12 ml, to draw blood from the patient 110 past the sampling site 161. The clinician can then take a sample of undiluted blood from the sampling site 161. Subsequently, the blood and other fluids drawn into the reservoir 130 during the sampling operation may be re-infused by depressing the plunger 164.

It should be noted that the pressure transducer 138 may include a flow restrictor or flow control means to prevent flushed solution from going proximally through the sensor rather than back to the patient 110. For example, the stopcock 136 may be used to close off the fluid path through the pressure transducer 138 prior to re-infusing the reservoir clearance volume. The entire sampling system 120 is thus closed as the "priming" volume that ensures a pure sample of blood reaches the sampling site 161 remains within the sampling system 120 and is re-infused into the patient. Further, in the flushing/priming mode, the reservoir 130, sample sites 161, and tubes can be flushed, cleared, and de-bubbled such that portions of the blood sampling-blood pressure monitoring system 100 may be cleared for operation, as previously described.

As has been described above, with respect to FIG. 1, an example of a blood sampling-blood pressure monitoring system 100 has been illustrated. In particular, as has been described, the blood sampling-blood pressure monitoring system 100 may include: a control value 132, a blood pressure transducer 138, a reservoir 130 with a plunger 164, a sampling site 161, and a blood pressure transducer 138 for measuring the blood pressure of the patient 110, which may be displayed on the display monitor 160. Further, as has been described, a tube may be connected from the patient 110 to the sampling sight 161, from the sampling sight 161 to the control valve 132, and from the control valve 132 to the pressure transducer 138, etc. In one embodiment, the control valve 132 may be a multi-port control valve that is described in detail in pending U.S. patent application Ser. No. 15/801,009, entitled "Multi-Port Control Valve for use in a Blood Sampling, Blood Pressure Measurement Systems", hereby incorporated by reference, or may be any suitable control valve presently utilized in blood sampling-blood pressure monitoring systems.

Figure 2:
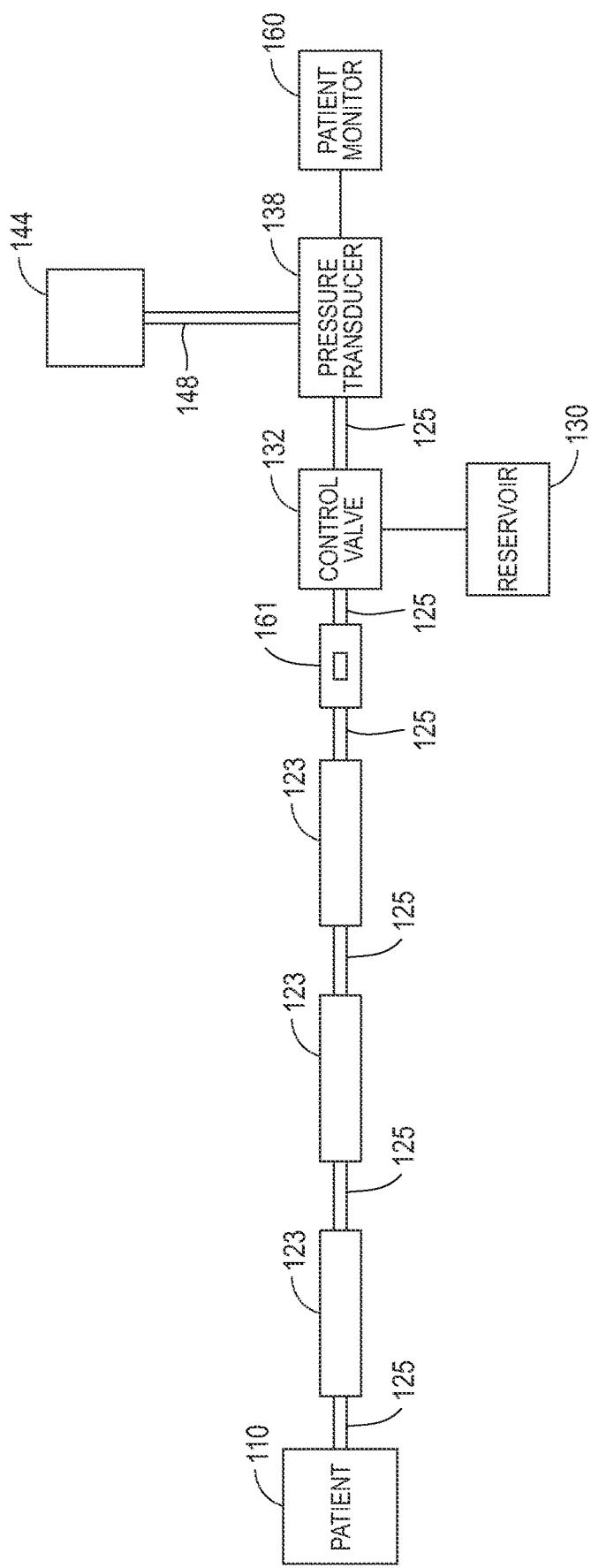
FIG. 2 is a diagram particularly illustrating the combination of flexible and rigid tubing sections, according to embodiments of the invention.

With additional reference to FIG. 2, in combination with FIG. 1, for illustrative purposes, in one embodiment, tubing between the patient 110 and the blood pressure transducer 138 may include flexible tubing sections interlinked with ridged tubing sections. As can be seen in FIGS. 1-2, a plurality of flexible tubing sections 125 may be interlinked with rigid tubing sections 123. In particular, the plurality of rigid tubing sections 123 and the plurality of flexible tubing sections 125 may be interlinked with one another between the patient 110 and the blood pressure transducer 138 for the blood pressure measurement of the patient 110 by the blood pressure transducer 138 to improve the signal quality for blood pressure measurement, as will be described. As has been previously described, the blood pressure measurement may be displayed on the patient monitor 160.

More particularly, the plurality of rigid tubing sections 123 and the flexible tubing sections 125 are interlinked with one another, one after another, between the patient 110 and the sampling site 161. It should be noted that, in this way, the pressure signal measured by the blood pressure transducer 138 at the back end is improved while allowing for an increase in the working length of system, as well as, maintaining the flexibility of the tubing from the pressure transducer 138 and the patient 110 (via the flexible tubing sections 125).

As can be seen in FIGS. 1 and 2, the rigid tubing sections 123 may be longer than the flexible tubing sections 125. The flexible tubing sections 125 may be standardized tubing typically utilized in blood sampling-blood pressure monitoring systems. As an example, the standardized flexible tubing 125 may be a polyvinyl chloride (PVC). The rigid tubing sections 123, on the other hand, may be utilized as replacement parts for the typical standardized flexible tubing sections to improve the pressure signal for blood pressure measurement by the pressure transducer 138, as previously described.

In particular, the flexible tubing sections 125 may have a relatively low tensile modulus and may be relatively flexible whereas the rigid tubing sections 123 may have a significantly higher tensile modulus than the flexible tubing sections 125 and may be relatively rigid. As examples, the flexible tubing sections 125 may be relatively flexible and may include one or more of the following material components: a flexible polymer, a flexible plastic, or a flexible polyvinyl chloride (PVC). On the other hand, the rigid tubing sections 123 may be relatively rigid and may include one or more of the following material components: a rigid polymer, a rigid plastic, a rigid polyvinyl chloride (PVC), a metal, a glass, metallic wires, metallic braids, aramid fibers, glass fibers, plastic fibers, or any suitable stiffer material.

As an example, rigid tubing sections 123 may be added in-line with standardized tubing 125 of an existing of blood sampling-blood pressure monitoring system 100. This may increase the working length of the tubing while maintaining the pressure signal fidelity to meet required performance specifications for blood pressure monitoring by the pressure transducer 138 for blood pressure monitoring systems. In particular, when rigid tubing sections 123 are utilized to replace parts of existing tubing, the pressure signal for blood pressure monitoring as measured by the pressure transducer 138 may be improved thereby increasing blood pressure monitoring accuracy. It should be appreciated that the longer sections of rigid tubing 123 may be joined together with shorter sections of existing (e.g., currently used) standard flexible tubing 125, forming a chain of sections of longer rigid tubing 123 and short sections of compliant tubing (e.g., standardized flexible tubing 125), forming a chain of longer sections of rigid tubing and short sections of compliant tubing to provide a rigid portion of tubing (e.g., ideal for pressure monitoring) while allowing the flexibility of the line (e.g., joined by the short compliant tubing 125). The series of rigid tubing sections 123 provide optimal conditions (e.g., high fidelity at the rigid sections) to improve the accuracy of blood pressure monitoring by the pressure transducer 138.

Figure 3:
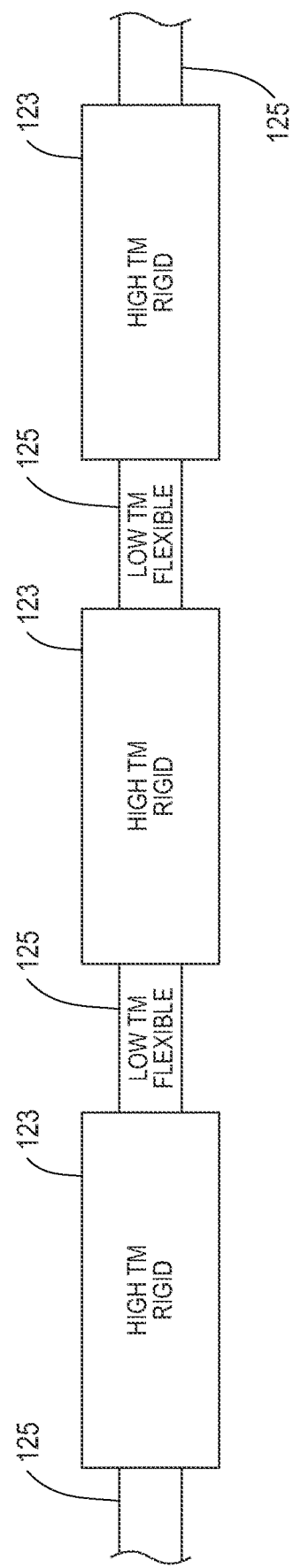
FIG. 3 is another diagram illustrating the combination of flexible and rigid tubing sections, according to embodiments of the invention.

With brief additional reference to FIG. 3, in combination with FIGS. 1 and 2, FIG. 3 illustrates that the longer rigid tubing sections 123 may have a relatively high tensile modulus (TM) whereas the shorter flexible tubing sections 125 may have a relatively low tensile modulus (TM). Therefore, as has been previously described, the standardized tubing sections 125 may have a relatively low tensile modulus and be flexible tubing (e.g., a flexible PVC) and the rigid tubing sections 123 may have a significantly higher tensile modulus and be rigid (e.g., a rigid PVC). As has been described, the flexible tubing sections 125 may be relatively flexible and may include one or more of the following material components: a flexible polymer, a flexible plastic, or a flexible polyvinyl chloride (PVC). On the other hand, the rigid tubing sections 123 may be relatively rigid and may include one or more of the following material components: a rigid polymer, a rigid plastic, a rigid polyvinyl chloride (PVC), a metal, a glass, metallic wires, metallic braids, aramid fibers, glass fibers, plastic fibers, or any suitable stiffer material. It should be appreciated that any suitable material may be used for flexible or rigid tubing that has an appropriate tensile modulus (TM).

It should be appreciated that the rigid tubing sections 123 interlinked with standardized tubing 125 to increase blood pressure monitoring accuracy, allowing for increased system length, while maintaining flexibility, similarly allows for all the modes of operation (e.g., a monitoring mode, a drawing/re-infusing mode, a sampling mode, or a flushing/priming mode) for the blood sampling-blood pressure monitoring system, as previously described.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A tubing system for use in a blood sampling-blood pressure monitoring system that includes a control valve, a reservoir with a plunger, a sampling site, and a blood pressure transducer configured to measure the blood pressure of a patient, the tubing system comprising:
   a plurality of flexible tubing sections; and
   a plurality of rigid tubing sections, wherein the plurality of rigid tubing sections and the flexible tubing sections are configured to be interlinked with one another between the patient and the blood pressure transducer for the blood pressure measurement of the patient, wherein, the plurality of rigid tubing sections and flexible tubing sections are configured to be fixedly interlinked with one another between the patient and the sampling site, the rigid tubing sections being longer than the flexible tubing sections, wherein the flexible tubing sections have a low tensile modulus and are flexible whereas the rigid tubing sections have a higher tensile modulus than the flexible tubing sections and are rigid, wherein the flexible tubing sections include a flexible polymer.

2. The tubing system of claim 1, wherein, the flexible polymer includes a flexible plastic.

3. The tubing system of claim 1, wherein, the rigid tubing sections include a rigid polymer.

4. The tubing system of claim 3, wherein, the rigid polymer includes a rigid plastic.

5. The tubing system of claim 1, wherein, the rigid tubing sections include a metal.

6. The tubing system of claim 1, wherein, the rigid tubing sections include a glass.

7. A blood sampling-blood pressure monitoring system comprising:
   a control valve;
   a reservoir with a plunger;
   a sampling site;
   a blood pressure transducer configured to measure the blood pressure of a patient, wherein the control valve is coupled to and controls fluid flow to the reservoir, the sampling site, and the blood pressure transducer; and
   a tubing system including:
   a plurality of flexible tubing sections; and
   a plurality of rigid tubing sections, wherein the plurality of rigid tubing sections and the flexible tubing sections are configured to be interlinked with one another between the patient and the blood pressure transducer for the blood pressure measurement of the patient, wherein, the plurality of rigid tubing sections and flexible tubing sections are configured to be fixedly interlinked with one another between the patient and the sampling site, the rigid tubing sections being longer than the flexible tubing sections, wherein the flexible tubing sections have a low tensile modulus and are flexible whereas the rigid tubing sections have a higher tensile modulus than the flexible tubing sections and are rigid, wherein the flexible tubing sections include a flexible polymer.

8. The blood sampling-blood pressure monitoring system of claim 7, wherein, the flexible polymer includes a flexible plastic.

9. The blood sampling-blood pressure monitoring system of claim 7, wherein, the rigid tubing sections include a rigid polymer.

10. The blood sampling-blood pressure monitoring system of claim 9, wherein, the rigid polymer includes a rigid plastic.

11. The blood sampling-blood pressure monitoring system of claim 7, wherein, the rigid tubing sections include a metal.

12. The blood sampling-blood pressure monitoring system of claim 7, wherein, the rigid tubing sections include a glass.

13. A method for utilizing a tubing system in a blood sampling-blood pressure monitoring system that includes a control valve, a reservoir with a plunger, a sampling site, and a blood pressure transducer configured to measure the blood pressure of a patient, the method comprising:

connecting a plurality of flexible tubing sections to a plurality of rigid tubing sections in such a manner that the plurality of rigid tubing sections and the flexible tubing sections are configured to be interlinked with one another between the patient and the blood pressure transducer for the blood pressure measurement of the patient, wherein, the plurality of rigid tubing sections and flexible tubing sections are configured to be fixedly interlinked with one another between the patient and the sampling site, the rigid tubing sections being longer than the flexible tubing sections, wherein the flexible tubing sections have a low tensile modulus and are flexible whereas the rigid tubing sections have a higher tensile modulus than the flexible tubing sections and are rigid, wherein the flexible tubing sections include a flexible polymer.

14. The method of claim 13, wherein, the flexible polymer includes a flexible plastic.

15. The method of claim 13, wherein, the rigid tubing sections include a rigid polymer.

16. The method of claim 15, wherein, the rigid polymer includes a rigid plastic.

17. The method of claim 13, wherein, the rigid tubing sections include a metal.

18. The method of claim 13, wherein, the rigid tubing sections include a glass.

\* \* \* \* \*